(12) United States Patent
Winarski

(10) Patent No.: US 8,666,672 B2
(45) Date of Patent: Mar. 4, 2014

(54) SYSTEM AND METHOD FOR INTERPRETING A USER'S PSYCHOLOGICAL STATE FROM SENSED BIOMETRIC INFORMATION AND COMMUNICATING THAT STATE TO A SOCIAL NETWORKING SITE

(75) Inventor: Tyson York Winarski, Tempe, AZ (US)

(73) Assignee: Radial Comm Research L.L.C., Dover, DE (US)

( * ) Notice: Subject to any disclaimer, the term of this patent is extended or adjusted under 35 U.S.C. 154(b) by 729 days.

(21) Appl. No.: 12/623,414

(22) Filed: Nov. 21, 2009

(65) Prior Publication Data

US 2011/0124977 A1 May 26, 2011

(51) Int. Cl.
*A61B 5/16* (2006.01)
*G06F 19/00* (2011.01)
*G06F 3/01* (2006.01)
*A61B 5/01* (2006.01)
*A61B 5/024* (2006.01)
*A61B 5/145* (2006.01)
*A61B 5/1455* (2006.01)
*A61B 5/053* (2006.01)

(52) U.S. Cl.
CPC ............ *G06F 19/3443* (2013.01); *G06F 3/011* (2013.01); *G06F 3/015* (2013.01); *G06F 2203/011* (2013.01); *A61B 5/165* (2013.01); *A61B 5/01* (2013.01); *A61B 5/024* (2013.01); *A61B 5/145* (2013.01); *A61B 5/1455* (2013.01); *A61B 5/0531* (2013.01)
USPC .............. 702/19; 600/301; 600/306; 600/549

(58) Field of Classification Search
CPC ................................................ G06F 2203/011
See application file for complete search history.

(56) References Cited

U.S. PATENT DOCUMENTS

| 6,151,571 | A * | 11/2000 | Pertrushin | 704/209 |
|---|---|---|---|---|
| 6,190,314 | B1 * | 2/2001 | Ark et al. | 600/300 |
| 7,020,508 | B2 * | 3/2006 | Stivoric et al. | 600/390 |
| 7,234,117 | B2 * | 6/2007 | Zaner et al. | 715/758 |
| 7,409,639 | B2 * | 8/2008 | Dempski et al. | 715/705 |

(Continued)

FOREIGN PATENT DOCUMENTS

WO    WO 2009/043020    *  2/2009  .............. H04L 29/08

OTHER PUBLICATIONS immod.com. "Your first time on imood.com". Electronic document. Apr. 15, 2000. 2 pages.*
Barreto, A., Zhai, J. & Adjouadi, M. in Human-Computer Interaction (Lew, M., Sebe, N., Huang, T. S. & Bakker, E. M.) 4796, 2938 (Springer Berlin Heidelberg, 2007).*

(Continued)

*Primary Examiner* — Soren Harward
(74) *Attorney, Agent, or Firm* — Stolowitz Ford Cowger LLP

(57) ABSTRACT

The present invention is a mood sensing and communicating system and method that includes a biometric sensor configured to sense biometric information from a person. A mood interpretive system is supported on a computing device or on a remote server. The mood interpretive system is in communication with the biometric sensor and is configured to assign a psychological or emotional mood state with the sensed biometric information. A communication system is supported on the computing device and is configured to communicate the assigned psychological mood state across an Internet to a web-site for positing on a web page. The method includes sensing biometric information from a user with a biometric sensor, associating a psychological mood state with the sensed biometric information with a mood interpretive module, and communicating the assigned psychological mood state to a web-site supported on a server across an Internet.

16 Claims, 6 Drawing Sheets

(56) References Cited

U.S. PATENT DOCUMENTS

| | | | |
|---|---|---|---|
| 8,019,875 B1* | 9/2011 | Nielsen | 709/227 |
| 8,160,549 B2* | 4/2012 | Bychkov et al. | 455/412.1 |
| 2002/0019586 A1* | 2/2002 | Teller et al. | 600/300 |
| 2004/0133081 A1* | 7/2004 | Teller et al. | 600/300 |
| 2005/0280545 A1* | 12/2005 | Ryou | 600/300 |
| 2006/0170945 A1* | 8/2006 | Bill | 358/1.13 |
| 2008/0082613 A1* | 4/2008 | Szeto et al. | 709/206 |
| 2008/0155080 A1* | 6/2008 | Marlow et al. | 709/223 |
| 2008/0214903 A1* | 9/2008 | Orbach | 600/301 |
| 2009/0012988 A1* | 1/2009 | Brown | 707/102 |
| 2011/0014932 A1* | 1/2011 | Estevez | 455/466 |

OTHER PUBLICATIONS

Kim, K. H., Bang, S. W. & Kim, S. R. Emotion recognition system using short-term monitoring of physiological signals. Medical & Biological Engineering & Computing 42, 419-427 (2004).*

Lisetti, C. L. & Nasoz, F. Using Noninvasive Wearable Computers to Recognize Human Emotions from Physiological Signals. EURASIP Journal on Advances in Signal Processing 2004, 1672-1687 (2004).*

Miluzzo, E., Lane, N. D., Eisenman, S. B. & Campbell, A. T. in Smart Sensing and Context (Kortuem, G., Finney, J., Lea, R. & Sundramoorthy, V.) 1-28 (Springer Berlin Heidelberg, 2007).*

Miluzzo, E. et al. Sensing meets mobile social networks. in ACM Conference on Embedded Network Sensor Systems 337-350 (ACM Press, 2008).*

* cited by examiner

SYSTEM AND METHOD FOR INTERPRETING A USER'S PSYCHOLOGICAL STATE FROM SENSED BIOMETRIC INFORMATION AND COMMUNICATING THAT STATE TO A SOCIAL NETWORKING SITE

FIELD OF THE INVENTION

This invention relates to systems that can interpret a psychological or emotional state of a person from sensed biometric information and communicate that state across an Internet to a social networking site.

BACKGROUND OF THE INVENTION

Social Networking Websites such as MYSPACE, FACEBOOK, and the like allow user-members to post their "mood" on their member-profile pages. These mood indicators can include psychological or emotional states such as being happy, sad, grumpy, frustrated, sleepy, stressed, relaxed, fussy, etc. Typically, these mood indicators are accompanied by a mood icon such as a yellow smiley face that displays the assigned mood. At present, user-members post their mood on their member-profile pages by manually selecting a mood from a menu. Manual selection of a mood allows user-members to post a mood that may not actually reflect their true mood.

SUMMARY OF THE INVENTION

The present invention is a mood sensing and communicating system that includes a biometric sensor configured to sense biometric information from a person. The system further includes a computing device. A mood interpretive module is supported on the computing device. The mood interpretive module is in communication with the biometric sensor and is configured to assign a psychological mood state with the sensed biometric information. A communication system is supported on the computing device and is configured to communicate the assigned psychological or emotional mood state across an Internet to a web-site for positing on a web page.

The present invention is also a method for sensing and communicating a user's mood. The method includes sensing biometric information from a user with a biometric sensor, associating a psychological or emotional mood state with the sensed biometric information with a mood interpretive module, and communicating the assigned psychological mood state to a web-site supported on a server across an Internet.

The present invention further includes a method for sensing and communicating a user's mood. The method includes sensing a vocal signature of a user with a microphone, associating a psychological mood state with the sensed vocal signature, storing the assigned psychological mood state in a memory, and communicating the assigned psychological mood state across a network to a web-site supported on a server.

Further aspects of the invention will become apparent as the following description proceeds and the features of novelty which characterize this invention are pointed out with particularity in the claims annexed to and forming a part of this specification.

BRIEF DESCRIPTION OF THE DRAWINGS

The novel features that are considered characteristic of the invention are set forth with particularity in the appended claims. The invention itself; however, both as to its structure and operation together with the additional objects and advantages thereof are best understood through the following description of the preferred embodiment of the present invention when read in conjunction with the accompanying drawings.

DETAILED DESCRIPTION OF THE INVENTION

This invention is described in preferred embodiments in the following description with reference to the Figures, in which like numbers represent the same or similar elements. While this invention is described in terms of the best mode for achieving this invention's objectives, it will be appreciated by those skilled in the art that variations may be accomplished in view of these teachings without deviating from the spirit or scope of the invention.

Figure 1:
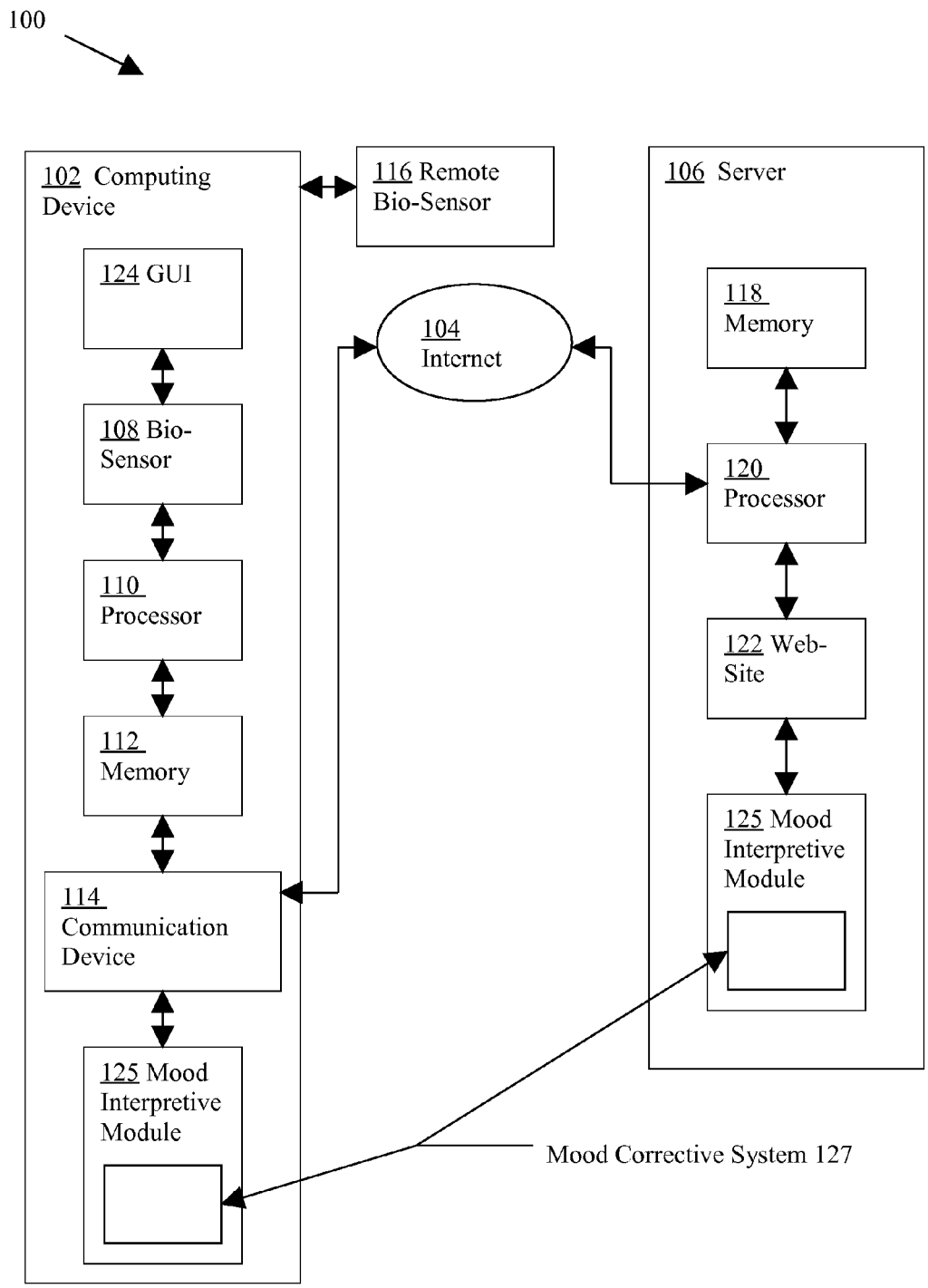
FIG. 1 illustrates a block diagram of a system for sensing and communicating a user's mood.

FIG. 1 illustrates a block diagram of a system 100 for sensing and communicating a user's mood. System 100 includes a computing device 102. Computing device 102 may be a cellular phone, a desktop computer, a laptop computer, a Personal Digital Assistant (PDA), a wireless device such as a BLACKBERRY or any other device that includes a processor 110 and memory 112 and is capable of communicating with a computer network. Computing device 102 is in communication with a server 106 through an Internet 104. Computing device 102 includes a bio-sensor 108, a processor 110, memory 112, a communication device 114, and a Graphical User Interface (GUI) 124. Communication device 102 may also be coupled to a remote bio-sensor 116. Processor 110 is in bidirectional communication with memory 112, communication device 114, bio-sensor 108, remote bio-sensor 116, and GUI 124. Bio-sensor 108 is housed within computing device 102. Remote bio-sensor 116 is coupled to processor 110 in computing device 102 through a connection such as a Universal Serial Bus (USB), FIREWIRE, a parallel port connection, BLUETOOTH, or other electrical communications link that allows for bidirectional communication.

Bio-sensors 108 and 116 are configured to sense biometric information from a person. Such biometric information can include body temperature, skin temperature, heart rate, blood oxygen levels, vocal signature, skin moisture, or other biological features of a person indicative of an emotional state. Bio-sensors 108 and 116 may include microphones on a cell phone that measure vocal signatures of a person when they are speaking during a phone call for example. Bio-sensors 108 and 116 may also include temperature sensors to measure a person's skin or body temperature. Bio-sensors 108 and 116 may devices that measure blood oxygen levels and heart rates such as lasers, or electrical contacts that measure electrical conductivity of a person. Bio-sensors 108 and 116 may include moisture detectors that measure a person's skin moisture.

Bio-sensors 108 are integrated with computing device 102. Bio-sensors 108 that are integrated with computing device 102 are highly desirable for computing devices that are portable such as cellular phones, PDA's, or other wireless and mobile devices. Bio-sensors 116 may be used with all computing devices 102, but most particularly desktop computers and laptop computers. Bio-sensors 116 may take the form of a being integrated in an existing device that is remotely coupled to a desktop or laptop computer such as a computer mouse, a keyboard, a microphone, or other remotely coupled device that is capable of housing bio-sensors 116.

Computing device 102 also includes a mood interpretive module 125. A person's psychological or emotional mood state may be determined through sensing biometric information from the person with bio-sensors 108 and 116. Such biometric information that can indicate a person's mood includes body temperature, skin temperature, heart rate, blood oxygen levels, vocal signature, skin moisture, or other biological features of a person. For example, psychological mood states such as happiness, sadness, excitement, anger, boredom, relaxation, stress, being tired, and other psychological mood states can be determined from sensing body temperature, skin temperature, heart rate, blood oxygen levels, vocal signature, skin moisture, or other biological features of a person. While a psychological mood state can be inferred from any single biometric indicator, more sophisticated determinations of a person's psychological mood state can be determined by measuring multiple biometric indicators and combining those results to assign a psychological mood state.

Mood interpretive module 125 is supported on computing device 102 and is in unidirectional or bidirectional communication with bio-sensors 108 and 116. Sensors are typically unidirectional communication devices, but could be bidirectional if their sensitivity is adjusted by processor 110. Mood interpretive module 125 receives biometric information sensed by bio-sensors 108 and 116. Mood interpretive module 125 then compiles the sensed biometric information and associates a psychological mood state to the sensed information. The mood interpretive module operates to find a single solution (i.e. a psychological mood state) to a system having multiple variables (i.e. different sensed biometric parameters). Methods of solving multiple variable systems for a single solution are well known and exist in many varieties, such as equations, matrices, neural networks, and other methods. Exemplary processes of assigning a psychological mood state to the sensed information are provided in FIGS. 5 and 6. Mood interpretive module 125 may, for example, have the form of a neural network that assigns specific psychological mood states to one or more sensed biometric parameters. Mood interpretive module 125 may also take the form of a matrix formed of psychological mood states and biometric parameters. Specific mood states are determined in this embodiment by matching sensed biometric information to specific mood states in the matrix. Mood interpretive module 125 may include a mood corrective system 127. The mood corrective system 127 allows a user to manually review the operation of the mood interpretive module 125 and manually adjust the psychological mood states selected by the mood interpretive system 125 in response to the sensed biometric information. Mood corrective system 127 includes a touch-screen GUI that allows a user to manually associate ranges of sensed biometric information with psychological mood states. When bio-sensors 108 or 116 are in continuous contact with a user, mood interpretive system 125 may be programmed to periodically take readings from bio-sensors 108 or 116 to periodically update the psychological mood state of the user in real time. These periodic updates by mood interpretive system 125 may be periodically updated to web-site 122 through communications device 114.

Internet 104 may take the form of any computer network that allows for the communication of information between computing device 102 and server 106. Server 106 includes memory 118, a processor 120 and a web-site 122. Computing device 102 includes communication device 114. Communication device 114 is in communication with server 106 through Internet 104. The specific psychological mood state assigned to the sensed biometric information by mood interpretive module 125 is communicated to communication device 114. Communication device 114 then communicates the assigned psychological mood state to server 106 across Internet 104. The communication device 114 uploads the psychological mood state to web-site 122.

Figure 3:
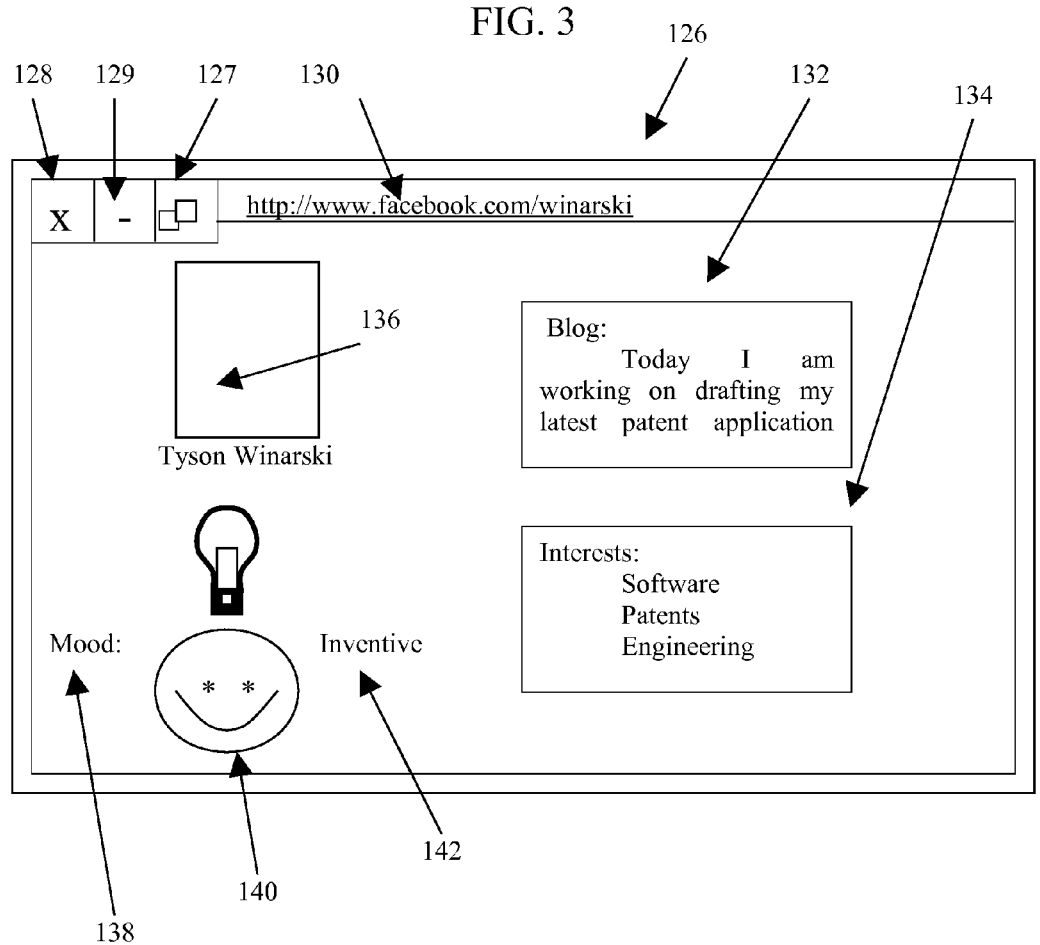
FIG. 3 illustrates a screen shot from a graphical user interface depicting a web-site screen of a user-member profile from a social networking site.

Web-site 122 is a social networking web-site such as FACEBOOK, MYSPACE, or other social networking site. These social networking sites include user-member pages that provide personal information about the user-member. An exemplary screen shot of such a user-member web-page 126 is shown in FIG. 3. One of the typical features of these social networking sites is for user-members to post their psychological mood state. At present, user-members manually select their psychological mood states directly on web-site 122 from a drop down menu. By using bio-sensors 108 and 116 together with mood interpretive module 125, the present invention allows for computing device 102 to accurately determine a user-member's mood directly from sensed biometric information taken from the user-member.

Figure 2:
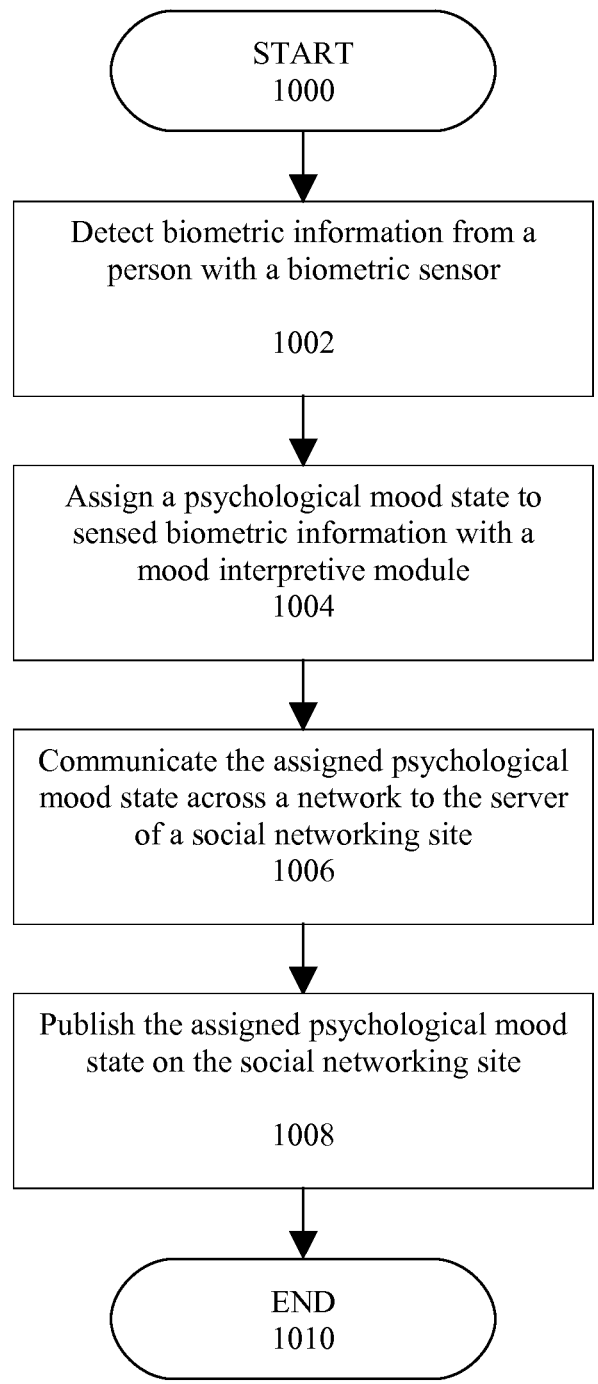
FIG. 2 illustrates a flow chart depicting a process for sensing and communicating a user's mood.

FIG. 2 illustrates a flow chart depicting a process for sensing and communicating a user's mood. The process begins with START 1000. In step 1002, biometric information of a user is sensed using biometric sensors 108 or 116. In step 1004, mood interpretive module 125 assigns a psychological mood state to the biometric information sensed with biometric sensors 108 or 116 by correlating the measured information with baseline information in order to pick the correct mood. In step 1006, mood interpretive module 125 communicates the assigned psychological mood state to communication device 114, which then communicates the assigned psychological mood state to web-site 122 across Internet 104. In step 1008, the psychological mood state is published on social networking web-site 122, as shown in FIG. 3. The process then ENDS in step 1010.

FIG. 3 illustrates a screen shot from a graphical user interface depicting a web-site screen 126 of a user-member profile from a social networking site. Screen 126 includes a menu bar 128 providing an "X" to allow a user to exit the screen 126, a "-" 129 to allow a user to minimize the screen 126, and a pair of overlapping squares 127 allowing a user to alter the size of screen 126. Screen 126 further includes a web address 130, which in this case points to a user-member webpage at the FACEBOOK web-site 122. Screen 126 shows the user-member's name and picture 136, a posted blog 132 by the user-member, and a listing of interests 134. In section 138, the psychological mood state of the user-member is shown. In this example, the user-member indicates that his psychological mood state is "inventive," as shown by text 142. This psychological mood state text indicator 142 is accompanied by an icon 140 signifying the inventive mood state, as illustrated by a smiley face having a light bulb hovering over head.

Figure 4:
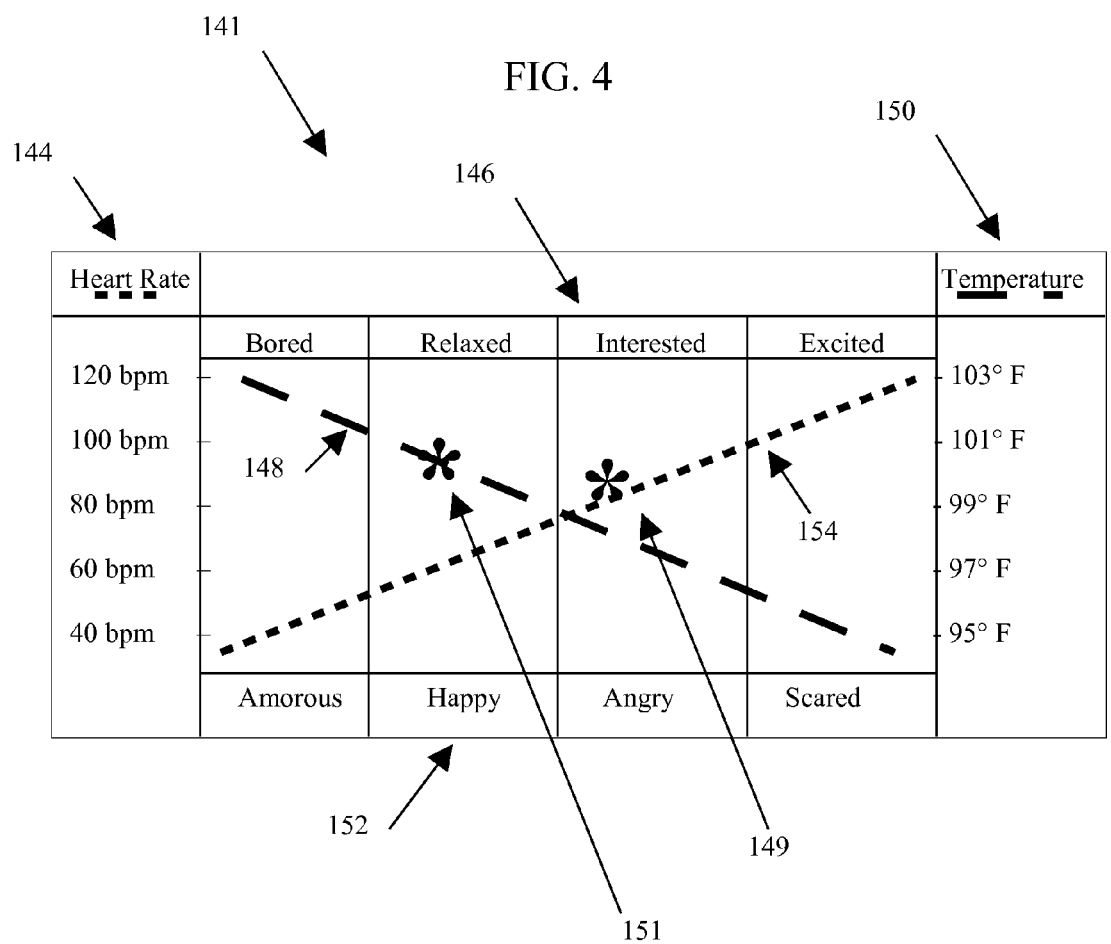
FIG. 4 illustrates a graphical representation of a mood interpretive module associating biometric information with psychological mood states.

FIG. 4 illustrates a graphical representation 141 of a mood interpretive system 125 associating biometric information with psychological or emotional mood states. While FIG. 4 shows a graphical representation 141, the information in graphical representation 141 could be alternately displayed in a matrix. In representation 141, biometric information sensed by bio-sensors 108, or 116 includes heart rate 144 and body temperature 150 as illustrated by data points 149 and 151. Mood states 146 and 152 are respectively associated with heart rate 144 and body temperature 150 as correlated with data points 149 and 151. Mood interpretive module 125 includes a baseline model of biometric information that is associated with mood states, as illustrated by temperature and heart baselines 148 and 154. While shown using baselines, mood interpretive module 125 may include any baseline model to support mood interpretive module 125 in making initial determinations as to associating emotional states with sensed biometric information. Mood interpretive module 125 utilizes graphical representation 141 to associate sensed biometric information, illustrated by data points 149 and 151, with mood states 146 and 152 with the aid of temperature and heart baselines 148 and 154. The psychological mood state 146 and 152 assigned to the sensed biometric mood state by mood interpretive system 125 is then transferred to communication device 114 for communication to server 106. Note that mood interpretive module 125, while illustrated as a part of computing device 102, may alternately be a supported on server 106. In a system where mood interpretive module 125 is supported on server 106, communication device 114 would communicate the information detected by sensors 108 and 116 to server 106 for processing by mood interpretive module 125.

Figure 5:
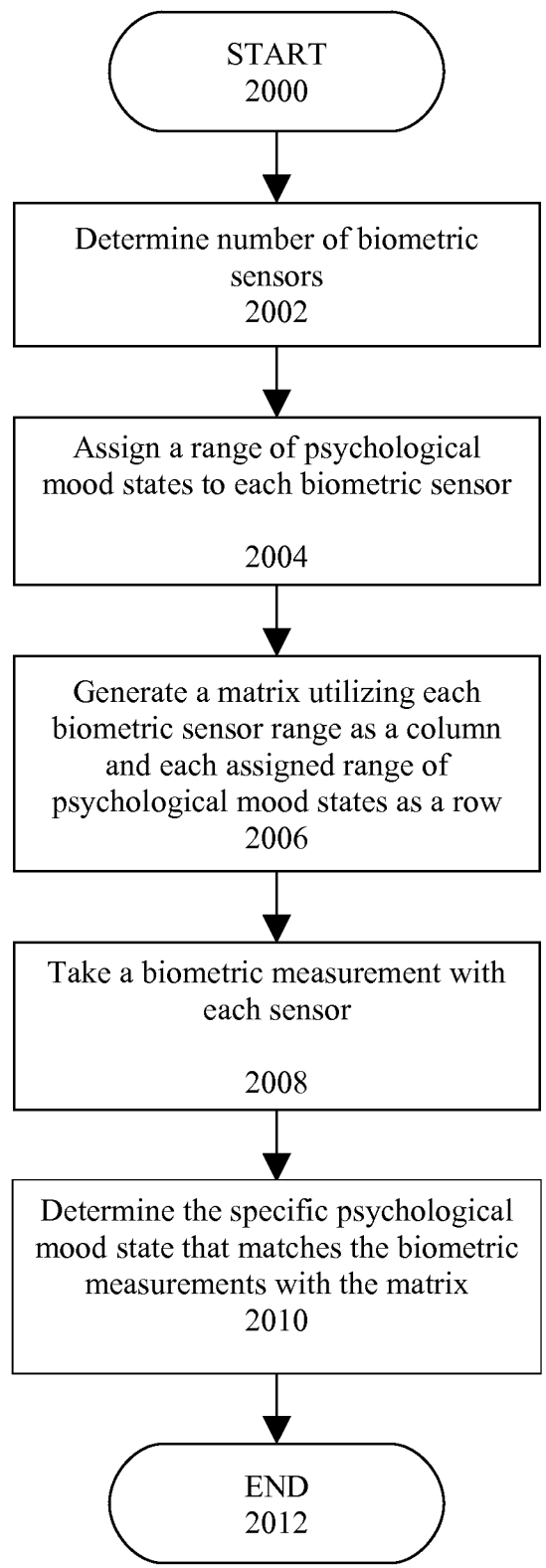
FIG. 5 illustrates a flow chart depicting a process for associating biometric information with a specific psychological mood state.

FIG. 5 illustrates a flow chart depicting a process for associating biometric information with a specific psychological mood state. The process begins with START 2000. In step 2002, mood interpretive module 125 determines the number of biometric sensors 108 and 116 and the number of different biometric parameters measured by sensors 108 and 116. In step 2004, mood interpretive module 125 assigns a range of psychological mood states (i.e. happy-bored-angry-sad) to each different biometric parameter (i.e. heart rate, body temperature, etc.). In step 2006, mood interpretive module 125 generates a matrix utilizing each biometric sensor parameter as a column and each assigned range of psychological mood states as a row. In step 2008, computer device 102 utilizes bio-sensors 108 and 116 to take biometric measurements of the user-member. In step 2010, mood interpretive module 125 utilizes the sensed biometric information together with the matrix generated in step 2006 to assign a specific psychological mood state to the sensed biometric information. The process ENDS in step 2012. The specific psychological mood state assigned in the process of FIG. 5 is then communicated to server 106 as shown in FIG. 2 in steps 1006 and 1008.

Figure 6:
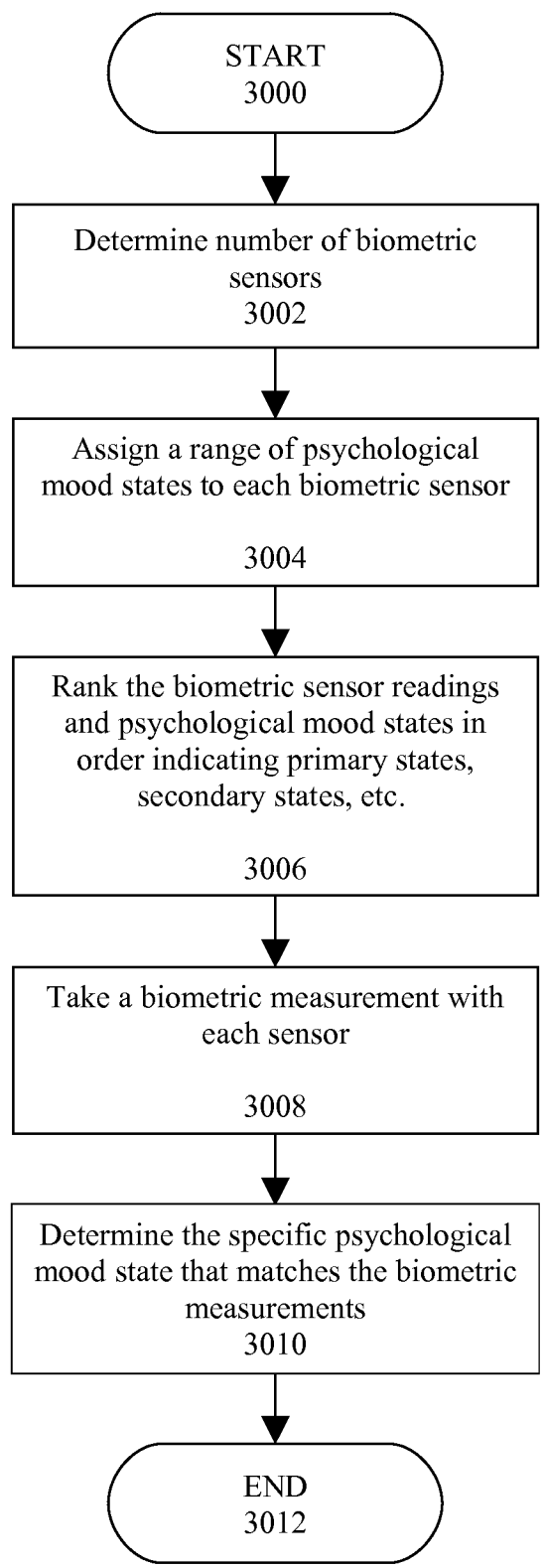
FIG. 6 illustrates a flow chart depicting an alternate process for associating biometric information with a specific psychological mood state.

FIG. 6 illustrates a flow chart depicting an alternate process for associating biometric information with a specific psychological mood state. The process begins with step 3000. In step 3002, mood interpretive module 125 determines the number of biometric sensors 108 and 116 and the number of different biometric parameters measured by sensors 108 and 116. In step 3004, mood interpretive module 125 assigns a range of psychological mood states (i.e. happy-bored-angry-sad) to each different biometric parameter (i.e. heart rate, body temperature, etc.). In step 3006, mood interpretive module 125 ranks the biometric sensor parameters and psychological mood states in an order. For example, mood interpretive module 125 may assign body temperature as designating a person's primary mood, such as happy, angry, or sad. Mood interpretive module 125 may then designate heart rate as a secondary mood indicator designating the type of primary mood that they are in. For example, if the user-member is happy, a slow heart rate may show that they are happily-relaxed, a fast heart rate may show that they are happily-excited. Alternatively, if the user-member is sad as indicated by their primary biometric parameter, body temperature in this example, a slow heart rate may indicate that they are sad and brooding, while a fast heart rate may show that they are sad and panicking Mood interpretive system 125 may access additional bio-sensor readings to provide tertiary, etc. refinements to determining the user-member's specific mood state. In step 3008, computer device 102 takes biometric measurements with bio-sensors 108 and 116. In step 3010, mood interpretive module 125 determined the psychological mood state from the sensed biometric information using the rankings generated in step 3006. In step 3012, the process ENDS. The specific psychological mood state assigned in the process of FIG. 6 is then communicated to server 106 as shown in FIG. 2 in steps 1006 and 1008.

While the preferred embodiments of the present invention have been illustrated in detail, it should be apparent that modifications and adaptations to those embodiments may occur to one skilled in the art without departing from the scope of the present invention as set forth in the following claims.

I claim:

1. A method comprising:
   selecting a primary biometric parameter and a secondary biometric parameter, the primary and secondary biometric parameters being two different parameters selected from the group consisting of body temperature, skin temperature, heart rate, blood oxygen levels, and skin moisture;
   creating a first linear correlation between biometric information of the primary biometric parameter and an ordered range of primary mood states;
   creating a second linear correlation between biometric information of the secondary biometric parameter and an ordered range of secondary mood states;
   receiving primary biometric information for the primary biometric parameter from a first sensor;
   interpreting the primary biometric information using the first linear correlation, thereby determining a primary mood state of a person;
   receiving secondary biometric information for the secondary biometric parameter from a second sensor;
   interpreting the secondary biometric information using the second linear correlation, thereby determining a secondary mood state of the person;
   using a processor to determine a specific psychological mood state of the person, which comprises the primary mood state and secondary mood state;
   communicating the specific psychological mood state to a server.

2. The method of claim 1, further comprising:
   selecting a tertiary biometric parameter, the tertiary biometric parameter being a different parameter from the primary biometric parameter and the secondary biometric parameter, and further being selected from the group consisting of body temperature, skin temperature, heart rate, blood oxygen levels, and skin moisture;
   creating a third linear correlation between biometric information of the tertiary biometric parameter and an ordered range of tertiary mood states;
   receiving tertiary biometric information for the tertiary biometric parameter from a third sensor; and interpreting the tertiary biometric information using the third linear correlation, thereby determining a tertiary mood state of the person;

and wherein the specific psychological mood state of the person further comprises the tertiary mood state.

3. The method of claim 1, further comprising periodically repeating the steps of sensing primary biometric information, interpreting the primary biometric information, sensing secondary biometric information, interpreting the secondary biometric information, determining a specific psychological mood state, and communicating the specific psychological mood state.

4. The method of claim 1, wherein the ordered range of primary mood states or the ordered range of secondary mood states comprise one or more of happy, sad, relaxed, angry, stressed, tired, excited, or combinations thereof.

5. The method of claim 1, further comprising allowing manual adjustment of the first linear correlation or the second linear correlation.

6. The method of claim 1, further comprising allowing manual adjustment of the specific psychological mood state.

7. The method of claim 1, wherein the server is part of a social networking website.

8. A system comprising:
a processor; and
a memory, comprising
   a first linear correlation between biometric information of a primary biometric parameter and an ordered range of primary mood states;
   a second linear correlation between biometric information of a secondary biometric parameter and an ordered range of secondary mood states; and
   instructions that, when executed, cause the processor to:
      receive primary biometric information from a first sensor configured to sense the primary biometric parameter;
      interpret the primary biometric information using the first linear correlation, thereby determining a primary mood state of a person;
      receive secondary biometric information from a second sensor configured to sense the secondary biometric parameter;
      interpret the secondary biometric information using the second linear correlation, thereby determining a secondary mood state of the person;
      determine a specific psychological mood state of the person, which comprises the primary mood state and secondary mood state; and
      communicate the specific psychological mood state to a server;
wherein the primary biometric parameter and the secondary biometric parameter are two different parameters selected from the group consisting of body temperature, skin temperature, heart rate, blood oxygen levels, and skin moisture.

9. The system of claim 8, further comprising a sensor configured to sense the primary biometric parameter.

10. The system of claim 8, further comprising a sensor configured to sense the secondary biometric parameter.

11. The system of claim 8,
wherein the memory further comprises:
   a third linear correlation between biometric information of a tertiary biometric parameter and an ordered range of tertiary mood states; and
   instructions that, when executed, cause the processor to:
      receive tertiary biometric information from a third sensor configured to sense the tertiary biometric parameter; and
      interpret the tertiary biometric information using the third linear correlation, thereby determining a tertiary mood state of the person;
wherein the tertiary biometric parameter is different from both the primary and secondary biometric parameters, and selected from the group consisting of body temperature, skin temperature, heart rate, blood oxygen levels, and skin moisture; and
wherein the specific psychological mood state of the person further comprises the tertiary mood state.

12. The system of claim 8, wherein the processor, the memory, and one or more sensors are housed within a cellular phone.

13. The system of claim 8, further comprising a touch-screen graphical user interface.

14. The system of claim 11, wherein the memory further comprises instructions that allow manual adjustment of the first linear correlation or the second linear correlation through the touch-screen graphical user interface.

15. The system of claim 11, wherein the memory further comprises instructions that allow manual adjustment of the specific psychological mood state through the touch-screen graphical user interface.

16. The system of claim 8, wherein the ordered range of primary mood states or the ordered range of secondary mood states comprise one or more of happy, sad, relaxed, angry, stressed, tired, excited, or combinations thereof.

* * * * *